US008753115B2

(12) United States Patent  
Schlottig et al.

(10) Patent No.: US 8,753,115 B2  
(45) Date of Patent: Jun. 17, 2014

(54) DEVICE AND METHOD FOR THE AMELIORATION OF RECESSES

(75) Inventors: Falko Schlottig, Füllinsdorf (CH); Uwe Werner, Uitikon Waldegg (CH)

(73) Assignee: Nexilis AG, Grenchen (CH)

( * ) Notice: Subject to any disclaimer, the term of this patent is extended or adjusted under 35 U.S.C. 154(b) by 509 days.

(21) Appl. No.: 12/993,799

(22) PCT Filed: May 13, 2009

(86) PCT No.: PCT/EP2009/055753  
§ 371 (c)(1), (2), (4) Date: Nov. 19, 2010

(87) PCT Pub. No.: WO2009/141252  
PCT Pub. Date: Nov. 26, 2009

(65) Prior Publication Data  
US 2011/0077696 A1    Mar. 31, 2011

(30) Foreign Application Priority Data

May 21, 2008  (CH) ...................................... 0760/08

(51) Int. Cl.  
*A61C 19/04*  (2006.01)
(52) U.S. Cl.  
USPC ............. 433/72; 433/173; 156/73.1; 156/293
(58) Field of Classification Search  
USPC ........................ 433/72, 74–75, 80, 82, 86–88; 606/86 R, 93–94, 96, 92, 95, 300–321, 606/331; 264/71; 24/691; 411/82.5; 156/73.1, 293  
See application file for complete search history.

(56) References Cited

U.S. PATENT DOCUMENTS

| 4,100,954 A * | 7/1978 | Muller et al. ................... 411/23 |
| 2009/0131947 A1* | 5/2009 | Aeschlimann et al. ......... 606/93 |
| 2011/0062617 A1* | 3/2011 | Lehmann et al. ............... 264/71 |

FOREIGN PATENT DOCUMENTS

| WO | 2008/034277 A2 | 3/2008 |
| WO | 2008/034278 A1 | 3/2008 |

(Continued)

OTHER PUBLICATIONS

Extended European Search Report corresponding to European Patent Application No. 11174531.1, dated Sep. 23, 2011.

(Continued)

*Primary Examiner* — Cris L Rodriguez  
*Assistant Examiner* — Edward Moran  
(74) *Attorney, Agent, or Firm* — Sughrue Mion, PLLC (57) ABSTRACT

The invention relates to a device (1) for the amelioration of a recess (8), e.g. a recess in a (human) bone (7). The device comprises an element (2) for producing or coupling mechanical energy, and a cylindrical collar (4) comprising a cylindrical lateral surface having an outside diameter and having a central recess (26) for accommodating a guide pin (3). The guide pin (3) is provided to be inserted substantially down to the base of the recess (8) before applying oscillations, and in the region of the end thereof facing the base of the recess it is surrounded by an amelioration sleeve (6) made from a material that can be liquefied by way of ultrasonic oscillations. The cylindrical lateral surface of the amelioration sleeve (6) substantially has the same outside diameter as the collar (4), and the guide pin (3) is accommodated in the central recess (26) in a displaceable manner such that the collar (4) upon applying ultrasonic oscillations can be displaced relative to the guide pin (3) in the direction toward the base of the recess (8) while liquefying and laterally and/or longitudinally displacing the material of the amelioration sleeve (6).

6 Claims, 6 Drawing Sheets

(56) References Cited

FOREIGN PATENT DOCUMENTS

| WO | 2008/128367 | A1 | 10/2008 |
| WO | 2009/052644 | A1 | 4/2009 |
| WO | 2010045751 | A1 | 4/2010 |

OTHER PUBLICATIONS

International Search Report of PCT/EP2009/005753 dated Sep. 29, 2009.

* cited by examiner

DEVICE AND METHOD FOR THE AMELIORATION OF RECESSES

TECHNICAL FIELD

The present invention relates to a device for the amelioration of a recess, particularly of a recess in a porous or perforate material having cavities freed by the recess, for example wood, technical material, human or animal bone, etc., and to elements of such devices, and to sterile packages comprising such elements. It further relates to methods for the amelioration of recesses in porous or perforate materials having cavities freed by the recess, for example in human or animal bone, particularly in jaw bone or spinal column bone.

PRIOR ART

Particularly from the field concerned with securing implants in recesses in the human or animal body, for example in drilled holes in bones, it is known to screw implants, which for example are provided with a self-tapping thread, into such recesses under application of force and then to wait for the implant to become incorporated in the bone.

It is likewise known, particularly in the case of recesses provided in especially porous bone sections, that the primary stability may be insufficient, that is to say the stability of the implant in the recess immediately after being screwed in, that is to say before the actual incorporation process has ended.

In order to solve such problems, it has already been proposed (see, for example, EP 1 363 543) to produce the implant at least partially or even completely from a material that can be liquefied by mechanical energy. The liquefiable material can be liquefied by mechanical oscillations after the implant has been inserted into the tissue area, and in this way a form-fit connection is produced between bone and implant by virtue of the liquefied and thereafter resolidified material. A disadvantage of such solutions is the fact that very specific implants are needed to be able to carry out such methods. A further disadvantage is that the liquefiable material cannot be introduced in a sufficiently targeted manner into the desired areas and often disappears, for example, in large recesses arranged at the bottom of the recesses, without in the end contributing to the actual primary stabilization.

The concept of filling recesses in a human body with the aid of a liquefiable material has in principle been known for some time, particularly in the dental field. Thus, U.S. Pat. No. 3,919,775 describes a method for filling and preparing openings with the aid of a liquefiable material which is initially pressed into the opening and which is then liquefied with the aid of a sonotrode, that is to say a device with which mechanical energy in the form of ultrasound can be introduced. The liquefied material then flows into cavities adjoining the recess and closes these cavities. In other fields where technical materials such as wood, plastics, foams, etc. are processed, such techniques are also known in the widest sense.

DISCLOSURE OF THE INVENTION

The object of the invention is accordingly to make available a device for the amelioration of a recess. The device is intended in particular to be suitable for preparing recesses in a porous material, or in a material formed with holes or cavities adjoining the recess, for further working. This particularly involves preparing recesses or (blind) holes or through-openings in wood or wood-like materials, porous plastics, or foam material, particularly a polymer foam, a composite foam and/or a metal foam, but also in human or animal bone, for example preparing such recesses for the subsequent securing of securing means or implants (also including the securing of pins or tendons, or the anchoring of artificial joints, for example hip, finger, shoulder, etc.), such that, in the case of non-human or non-animal material, the additional use of adhesives can be avoided and, in the case of bone material, a rapid primary stabilization of the implant is ensured. On the other hand, the amelioration is also intended to be suitable for as it were sealing such a recess, as may be of interest in endodontics, for example, in connection with the closure of root canals.

This object is achieved by the fact that such a device, which has an element for generating or coupling in mechanical energy, particularly vibration energy or oscillation energy, for example ultrasonic oscillations, also has a cylindrical collar with cylindrical jacket surface having an external diameter and having a central recess for receiving a guide pin. The guide pin is provided, and in particular arranged in the recess, so as to be inserted substantially as far as the bottom of the recess before mechanical energy, particularly in the form of oscillations, is applied (or so as to be caught at least in the area of the bottom of the recess, for example in a guide taper), thereby ensuring optimal guiding of the tool. The guide pin, in the area of the end thereof directed toward the bottom of the recess, is surrounded by an amelioration sleeve made from a material that can be liquefied by mechanical energy, particularly by oscillation energy, preferably ultrasonic oscillations. The (circular) cylindrical jacket surface of the amelioration sleeve has substantially the same external diameter as the collar, and the guide pin is received movably in the central recess such that, when mechanical energy is applied, preferably in the form of ultrasonic oscillations, the collar can be moved relative to the guide pin in the direction toward the bottom of the recess while liquefying and laterally and/or longitudinally displacing the material of the amelioration sleeve.

The guide pin is received movably in the central recess in a manner preferably virtually free of play, that is to say the external diameter of the guide pin corresponds substantially to the internal diameter of the central recess and is only smaller to the extent that the guide pin can be moved longitudinally in the recess. The difference between the external diameter of the guide pin and the internal diameter of the recess should therefore not be greater than 0.001 mm or 0.01 mm; the upper limit, e.g. in applications in the field of implants, is normally 0.1-0.5 mm or 0.2-0.3 mm.

One of the core aspects of this device is therefore, on the one hand, to provide a guide pin which can be pushed into the depth of the recess and can ensure the subsequent guiding of the tool. The guide pin thus serves, on the one hand, for optimal positioning of the tool in the depth of the recess. However, on the other hand, the guide pin also serves to guide the collar, which surrounds the guide pin as it were in the upper area (at the start of the process). At the start of the process, the amelioration sleeve, arranged below the collar, likewise surrounds the guide pin.

The amelioration sleeve preferably has an external diameter which is the same as (or possibly very slightly smaller than) the external diameter of the collar. The recess is typically of cylindrical shape. It must be stressed here that although the expression "cylindrical shape" is to be understood as preferably a circular cylindrical shape (that is to say with a circular cross section perpendicular to the main axis), it can also be understood as meaning shapes that have an oval or lenticular or elliptic cross section perpendicular to the main axis of the tool. In the field of implantology in particular, there are, on the one hand, recesses that are simply circular and have been produced by using a rotary drill, but there are also, for example in the case of dental applications, openings that are oval, lenticular or elliptic (for example in a defined and widened shape generated by drilling and then rasping), for example predefined by the shape of a tooth root. In the latter case, that is to say for oval, lenticular or elliptic openings, it is therefore possible to adapt the outer shape of both the collar and the amelioration sleeve to this for example oval-cylindrical recess. Moreover, other specific and rounded cross-sectional shapes, for example adapted to tooth roots, are also possible for the outer shape of the collar and of the amelioration sleeve.

By virtue of the fact that the collar is arranged movably on the guide pin in the context of the device, it is now possible, by applying the mechanical energy, e.g. the ultrasonic oscillations, and by suitable liquefying of the material of the amelioration sleeve, to introduce the material of the latter successively from the top downward into the porous areas, adjacent to the recess, of the material forming the recess. In this way, the cavities that could adversely affect the subsequent securing of a screw or of an implant in the recess are filled with the material of the amelioration sleeve in a very specific manner in the crucial area, in particular directly at the periphery of the recess, and this results in a huge increase in the primary stabilization. However, it is not absolutely necessary for a further element of any kind to be subsequently inserted into a recess that has been ameliorated in this way; it is also possible, by means of the proposed method and the proposed device, to as it were seal the recess only in a very specific manner in its peripheral area (compare the abovementioned uses in connection with endodontics).

As has already been mentioned above, a first preferred embodiment of the proposed device is accordingly characterized in that the external diameters of the collar and/or of the amelioration sleeve are substantially the same, or the latter diameter is only very slightly smaller, and in that this external diameter, moreover, is substantially the same as, or only very slightly less than, the internal diameter of the recess that is to be ameliorated. For the case of a non-circular cylindrical cross section, this is to be understood as meaning that the collar and/or the amelioration sleeve have substantially the same outer cross section, and the two elements are arranged relative to each other in such a way as to give a substantially smooth, i.e. stepless, transition. Thus, at the start of the process, the distal area (that is to say the area directed toward the bottom of the recess) of the tool, and also the entire area of the tool lying behind this in the recess, is already optimally positioned and guided. The amelioration sleeve typically has a height (along the axis of the recess) which is less than or equal to the depth of the recess, that is to say the amelioration sleeve, at the start of the process, disappears completely in the depth of the recess, and the collar also already engages partially in the upper area of the recess, or the amelioration sleeve (particularly when used in wood or other porous materials) ends flush with the upper edge of the material. Typically, the collar already engages by 5-50% in the recess before the ultrasound is applied.

It is also possible for the external diameter of the collar to be slightly larger than the internal diameter of the recess that is to be ameliorated (for example 0.5-2 mm larger). In this case, as the device is inserted, the recess that is to be ameliorated is widened slightly further and/or brought to the desired shape by the device. This can be of advantage particularly in the case of technical materials.

Another preferred embodiment of the proposed device is characterized in that the central recess is a circular cylindrical recess which is arranged coaxially with respect to the cylindrical jacket surface, in that the amelioration sleeve has a circular cylindrical recess for receiving the guide pin, and in that the guide pin has a circular cylindrical outer surface, wherein the internal diameters of said recesses are substantially the same as the external diameter of the guide pin.

Alternatively, however, other cross-sectional shapes in the central recess in the collar are also possible. For example, it is possible for the central recess to have an (isosceles) triangle shape, a square shape, or generally a polygonal shape (preferably with sides of equal length), wherein the points of such a cross-sectional shape can also reach as far as the external diameter of the collar. Thus, for example, more material can be deliberately provided in certain directions. The cross-sectional shapes can also be round generalized shapes; they can be concave or convex. Accordingly, the cross-sectional shape of the guide pin is of course analogous then, it generally being the rule that as small a gap as possible should be formed between the guide pin and the collar, so as to ensure that no liquefied material can enter the gap between these two materials. However, it is possible to very deliberately provide channels in this gap, which channels allow material to flow off deliberately if there is too high a pressure (for example if no cavities are present for the displacement of the material). Such channels can, for example, lead the liquefied material upward, that is to say in the direction out of the recess.

In order to distribute an optimal displacement of the material of the amelioration sleeve not only downward, but also radially outward into the peripheral area of the recess, it can be advantageous if the collar, at its distal end, has a preferably circumferential distal edge tapering toward said distal end, wherein this edge is preferably straight, and therefore conical, or curved, in particular concave or convex. This tapering edge ensures that the material not only experiences a displacement component in the direction of the bottom of the recess, but also a radial component. The angle of inclination of this tapering edge can be used, among other things, to determine the extent to which the material can be displaced in the radial direction (that is to say perpendicular to the central axis of the recess or perpendicular to the main axis of the tool) and longitudinal direction (that is to say in the direction toward the bottom of the recess and therefore parallel to the central axis of the recess or parallel to the main axis of the tool). If, for example, as little as possible is to be displaced toward the bottom of the recess (for example because this area is known to have large cavities that it is not desirable or necessary to fill), a very acute angle can be chosen (for example <45°, wherein the angle is defined as the angle between the central main axis of the collar and the inclined surface of the edge), with the result that a substantial radial component is obtained. However, if as much material as possible is to be distributed toward the bottom of the recess, an angle of greater than 45° can be chosen. In any event, this angle should preferably be less than or equal to 90° since, at greater angles, the material (although this may also be desirable) is pushed exclusively to the bottom.

The collar can also have a stepped design at the distal end. Since the collar is preferably attached directly to the sonotrode, it is advantageous if the wall thickness of the collar is not too small. Typically, the wall thickness of the collar should be in the range of 0.3-1 mm, preferably in the range of 0.5-0.8 mm, for typical applications in the medical field. On the other hand, it may be advantageous, for some applications, if the amelioration sleeve has a smaller wall thickness, to ensure that not too much material is introduced. The amelioration sleeve preferably has a wall thickness in the range of 0.1-1 mm, and it can also, for example, be only half as thick as the wall thickness of the collar. To take these conditions into account, it is possible for the amelioration sleeve to be hollowed out, preferably circumferentially hollowed out, on its inner face behind the distal end. Accordingly, this results in a smaller wall thickness of the amelioration sleeve, and a hollow space is obtained between guide pin and amelioration sleeve.

Alternatively, it is possible to design the amelioration sleeve of small wall thickness with an internal diameter that is greater than the external diameter of the guide pin, and to support the amelioration sleeve at the distal end by means of a special configuration of the guide pin. For this purpose, the guide pin then has, at the distal end, a flange which supports the thin amelioration sleeve on the inner face thereof. The flange then typically serves at the same time as an abutment for the collar. The flange can be formed all round the circumference, although it can also just have segments. If the flange is designed in the form of segments, it is also possible that the collar, with corresponding segments in the freed areas, engages as it were through this flange, when the collar is pushed to the distal end of the guide pin.

This flange can also be stepped, that is to say it can have, at its distal end, an external diameter that corresponds substantially to the external diameter of the collar, and, on the proximal face, it can have a circumferential step whose radial depth preferably corresponds to the thickness of the amelioration sleeve. The amelioration sleeve then lies in this step and is optimally positioned by the latter in the forward direction and radially inward direction.

With thin amelioration sleeves of this kind, it is then also preferably possible for the collar to have a stepped design at the distal end thereof, in which case, at the distal end of the collar, a cylindrical area of smaller external diameter is provided which engages in this hollow space of the amelioration sleeve or in the gap between amelioration sleeve and guide pin and is circumferentially surrounded by the amelioration sleeve of smaller wall thickness. This area of smaller external diameter preferably merges via an inclined flank into an area having the actual external diameter of the collar. In this inclined area, the amelioration sleeve is liquefied and the liquefied material is transported radially outward.

In the proposed device, the guide pin can preferably be pushed into the collar at most as far as an abutment position, so as to ensure that there is a defined end position for the method planned with the device. In this abutment position, the guide pin typically ends at most flush with the distal end of the collar, but preferably protrudes beyond this end. The protruding length in the abutment position is preferably at least 0.1-10 mm, particularly preferably 1-5 mm.

For good positioning of the guide pin in the area of the bottom of the recess, it can be advantageous if the guide pin tapers conically at its distal end and is preferably designed with a sharp tip, or it can be advantageous if the guide pin is rounded at this end. The rounding, or generally the configuration of the tip, can be adapted to the drill typically used for preparing the recess. If, for example, a drill is used that has an offset or a taper for guiding at the tip, then the guide pin preferably has an external diameter adapted to the diameter of this taper.

The device is preferably characterized in that the external diameter of the collar is in the range of 1-50 mm or even 1-80 mm, preferably in the range of 2-10 mm. It is also preferred that the external diameter of the guide pin is 0.1-20 mm less, preferably 0.5-10 mm less, particularly preferably 1-5 mm less, and in that the amelioration sleeve has a thickness such that the external diameter thereof is the same as the external diameter of the collar.

The element (the actual sonotrode) typically generates mechanical energy in the form of oscillation energy with a frequency in the range of 1 kHz-10 GHz. It is preferable for the oscillation energy to be introduced in the form of ultrasonic oscillations in the frequency range of 10 kHz to 10 GHz. A frequency range of 10 kHz-100 MHz is preferred, particularly preferably a range of 40 kHz-100 MHz. Ultrasonic oscillations in the range of 20-150 kHz, preferably in the range of 25-50 kHz, are normally used. These oscillations can be transmitted in the longitudinal direction (that is to say along the axis of the recess), transverse direction (that is to say radially with respect to the axis of the recess) or rotational direction (that is to say about the axis of the recess), or in a combination or linear combination of these directions, to the collar and/or guide pin and thus indirectly to the amelioration sleeve. The oscillations are preferably applied in the longitudinal direction, in which case, for example if an inclined flank is present at the distal end of the collar, this longitudinal oscillation permits a targeted transport of the liquefied material in the radial direction. Generally, the collar is preferably secured on the sonotrode, and the guide pin can be moved therein. Alternatively, it is possible for the guide pin to be secured on the sonotrode, and for the collar to be moved.

A preferred embodiment of the device is characterized in that the recess is a recess in an at least partially porous (human) bone section, particularly in a jaw bone or a spinal column bone, and in that the recess is preferably generated at least partially by preliminary drilling.

The amelioration sleeve is preferably made from a material that can be liquefied by said mechanical energy, particularly by oscillation energy, and that is selected from the following group: thermoplastic biocompatible polymers such as polyolefins (e.g. PP, LDPE, HDPE, UHMWPE), polyoxymethylene (POM), polyaryl ether ketones (e.g. PAEK, PEEK, PEKK), polycarbonates (PC), polyacrylates (e.g. PMMA), polyamides (PA), polyesters (e.g. PET, PBT), polysulfones and polyether sulfones (e.g. PSU, PES) and/or biodegradable or resorbable polymers, such as poly(L-lactide) (PLLA), poly (D,L-lactide) (PDLLA) and stereocopolymers thereof with a variable ratio of the L and D,L part, polyglycolides (PGA) and copolymers, such as polyglycolide-co-trimethyelene carbonate (PGA-co-TMC), poly(D,L-lactide-co-glycolide) (PDLLA-co-PGA) and poly(L-lactide-co-glycolide) (PLLA-co-PGA), poly(e-caprolactone), polydioxanones, trimethylene carbonates (TMC), polyorthoesters (POE) and other polyanhydrides, resorbable polymers which are produced from natural raw materials, such as modified polysaccharides (cellulose, chitin, dextran, starch), or a combination or a mixture of these materials. In principle, one or more pharmaceutical active substances can also be provided in this material or applied as a layer on this material, these generally being, for example, active substances for improving the incorporation process, for example for promoting bone growth, for preventing inflammation, etc. The material can in this case be specifically designed to release these pharmaceutical active substances in a controlled manner, that is to say in a controlled dose over a controlled period of time.

The material of the amelioration sleeve can be closed, but it can also be interrupted in different forms in each case, for example with holes or slits, in order to ensure that the amount of material to be introduced can, if necessary, be adapted to the anatomical circumstances or to the material density or specifically to the bone density/quality and thus to the cavities adjoining the recess.

The present invention also relates to a guide pin, with amelioration sleeve mounted and preferably even secured thereon (preferably until the above method is carried out), for a device of the kind described above. The amelioration sleeve can be secured in such a way that it can still be easily moved by the end user applying a certain force, in order to optimally position it for the final application. The amelioration sleeve can be secured on the guide pin in such a way that the distal end (or the front edge of the cylinder surface of the circumference) of the guide pin ends flush with the end of the amelioration sleeve or in such a way that, as is preferred, the distal end of the guide pin protrudes beyond the end of the amelioration sleeve, wherein the protruding length is preferably at least 1-10 mm, preferably 2-5 mm. This protruding length can then at least partially engage in the manner of a guide for example in the abovementioned taper of the recess that has been generated by a suitable drill.

A preferred embodiment of such a guide pin is characterized in that the collar is secured on the guide pin so as to be movable within defined limits (there are preferably a front, distal abutment and a rear, proximal abutment), and this overall unit has a coupling site for attachment to a sonotrode. Such a unit can then be made available, for example in a sterile state, and can be used simply by being attached to a hand-held appliance with a sonotrode.

In the case of such a guide pin, the circular cylindrical guide pin preferably has a diameter in the range of 0.5-50 mm, preferably in the range of 1-15 mm, particularly preferably in the range of 2-10 mm, and the cylindrical amelioration sleeve has a diameter that is greater by 0.1 to 20 mm, preferably by 0.2-10 mm or 0.5-10 mm, particularly preferably by 1-5 mm or 0.2-2 mm.

The present invention additionally relates to a sterile package with such a guide pin.

The present invention likewise relates to a method for operating a device of the kind described above. The method is preferably characterized in that the device, with mounted guide pin and mounted amelioration sleeve, is pushed into a recess which has optionally been pre-drilled (and possibly also rasped to give an oval shape for example) and which has an internal diameter corresponding substantially to the external diameter of collar and amelioration sleeve (the distance between recesses and collar or amelioration sleeve is preferably not more than 1 mm, preferably not more than 0.5 mm, particularly preferably not more than 0.1 mm), until the guide pin preferably abuts against the bottom of the recess and/or engages in a guide taper arranged at the bottom of the recess, and then, with simultaneous liquefying of the amelioration sleeve by applied mechanical energy, for example by applied ultrasound, and with pushing of the distal end of the collar into the recess, liquefied material is introduced into cavities, particularly lateral cavities, adjoining the recess. This applies equally to applications in bone and in other materials, for example wood or foam material, particularly polymer foam, composite foam and/or metal foam, etc.

The present invention finally relates to a method for the amelioration of a recess in a porous material, for example wood, plastic, or human or animal bone, using a device of the kind that has been described above. The method is preferably characterized in that the device, with mounted guide pin and mounted amelioration sleeve, is pushed into the recess which has optionally been pre-drilled (and which has possibly also been brought to a non-circular cross-sectional shape in an additional or simultaneous work step) and which has an internal diameter corresponding substantially to the external diameter of collar and amelioration sleeve, until the guide pin preferably abuts against the bottom of the recess and/or engages in a guide taper arranged at the bottom of the recess, and then, with simultaneous liquefying of the amelioration sleeve by applied mechanical energy, preferably by applied ultrasound, and with pushing of the distal end of the collar into the recess, liquefied material is introduced into cavities, particularly lateral cavities, adjoining the recess, wherein a securing means, a joint, a joint section, a tendon, an implant or a screw, etc., is then preferably screwed, if appropriate with partial self-tapping, into the ameliorated recess.

Other preferred embodiments of the invention are described in the dependent claims.

BRIEF EXPLANATION OF THE FIGURES

The invention is explained in more detail below on the basis of illustrative embodiments and with reference to the drawing, in which:

FIGS. 11 a)-e) show different cross-sectional designs of the guide pin in sectional views perpendicular to the central axis of the collar or of the amelioration sleeve, at a height where the amelioration sleeve is sectioned, wherein in a) a cylindrical central opening is shown, in b) a rectangular opening, in c) a hexagonal opening, in d) an octagonal opening and in e) a cross-shaped opening;

WAYS OF IMPLEMENTING THE INVENTION

The invention described in general terms above will now be explained in more detail with reference to the figures. The description now following is intended to support the claims and should not be used to limit them.

As a first illustrative embodiment of the present invention, we will describe how a device of the kind described above can be used to secure a dental implant. However, as has already been explained at the outset, an analogous method using an analogous device can equally be applied for forming recesses in wood, for example, or in other porous materials, such as foam material, particularly polymer foam, composite foam and/or metal foam, etc.

Figure 1:
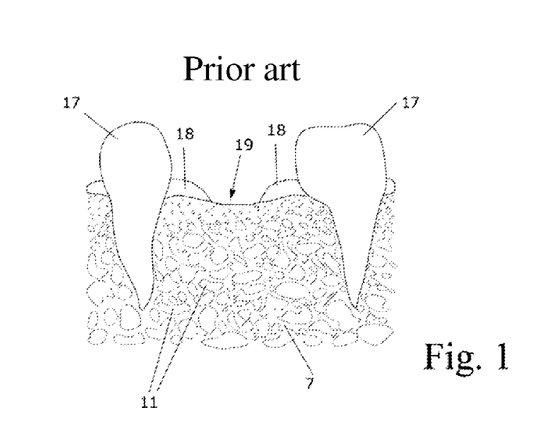
FIG. 1 shows a sectional view of an area, a gap in a row of teeth, in which an implant is to be fitted.

Thus, FIG. 1 shows a section through a jaw bone 7 in which, between two teeth 17, there is a gap 19 in which the gum 18 is also interrupted. The bone has as usual, particularly below the cortical substance (in what is called the trabecular or spongy area), a porous structure with cavities 11. An implant is to be fitted in such a gap 19. Typically, a bone of this kind has, in the trabecular or spongy area, a porosity in the range of 30-90%, that is to say the actual structure providing a load-bearing function, and thus suitable for a fixture, in some cases makes up only a small fraction of the volume.

Figure 2:
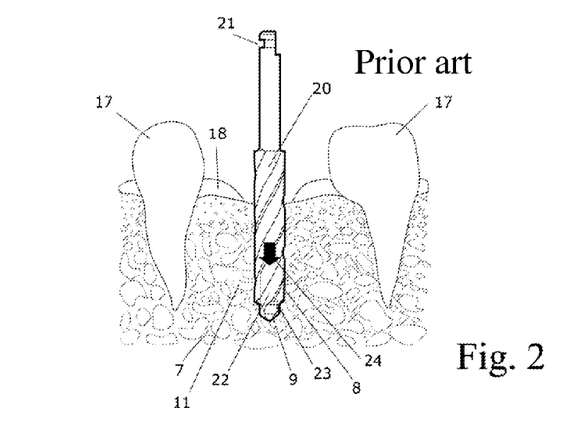
FIG. 2 shows a sectional view according to FIG. 1, phase of drilling/preliminary drilling of the recess for receiving the implant.

The procedure is accordingly one in which, in a first step, which is shown schematically in FIG. 2, a drill is used to prepare the actual recess for the implant. The drill 20 used in this illustrative embodiment has, at one end, a securing flange for the drive (drive not shown) and, at the other end, the actual drilling section, which generates the drilled hole, with the known turns 22 of the actual drill. This specific drill has a tapering portion at its tip, that is to say an area with a diameter smaller than the actual drill area, and, in the resulting recess, this tapering portion leads to a tapered bottom area in which the diameter is slightly smaller than in the area of the recess lying further up. The drill is, for example, a drill as described in WO 2004/080325.

As is indicated by the arrow 24, the drill, while rotating, is driven along its axis into the bone 7, and the actual recess 8 thus forms. Because this recess 8 is formed in porous bone, cavities 11 that adjoin the recess are, as it were, freed and opened in the peripheral area of the recess.

In a subsequent step, this recess 8 is now ameliorated so to speak, that is to say is either prepared for the securing of an implant in such a recess or is simply sealed in respect of the open cavities 11.

For this purpose, the proposed device (cf. FIG. 3) is in this case made ready by means of a procedure in which, in the case of the device 1 provided with a handle which has an element for generating ultrasound and on which a collar 4 (cylindrical tube section with central recess 26) is arranged via an upper attachment 25, a guide pin 3, with at its lower end an amelioration sleeve 6 surrounding the guide pin, is pushed into said recess 26 of the collar 4. It is possible, for example, that such guide pins 3 with amelioration sleeves 6 are presented in a holder 32 in different designs (for example different thicknesses of amelioration sleeves). The material of the amelioration sleeve is chosen such that it can be liquefied by application of mechanical energy, in particular of ultrasonic oscillations. The collar 4 has, at its distal end (that is to say at the end directed away from the handle 2), an edge 10 that tapers toward the tip. When the guide pin 3 is pushed in, this conical tip 10 engages in an undercut upper area (designated by reference sign 43) of the amelioration sleeve.

Figure 3:
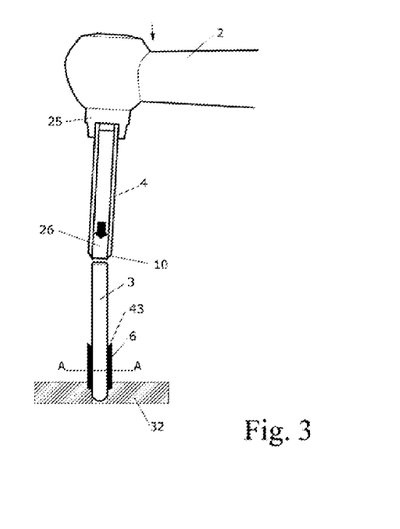
FIG. 3 shows a sectional view according to FIG. 1, phase of selecting the amelioration sleeve with guide pin and mounting it on a sonotrode or inserting it in a collar.

In connection with FIG. 3, it will be noted that, as is shown here, the guide pin and the amelioration sleeve can form a unit, although it is also possible for the collar, the guide pin and the amelioration sleeve to constitute a unit that is disposed of after one use. It is likewise possible that the collar and the amelioration sleeve, or other combinations of elements, form a unit that is disposed of after one use. These units can be presented in a sterile package.

As material for the amelioration sleeve, it is possible, for example, to use a resorbable polymer material of the Resomer type obtainable from Boehringer Ingelheim (Germany). It can be based on homopolymers of lactic acid (polylactide) or based on copolymers of lactic acid and glycolic acid, and it can also preferably be configured to ensure a controlled release of pharmaceutical active substances (for example active substances in general for improving the incorporation process, for example for promoting the growth of bone, for preventing inflammation, etc.) that are integrated in this material or are applied thereto.

Figure 4:
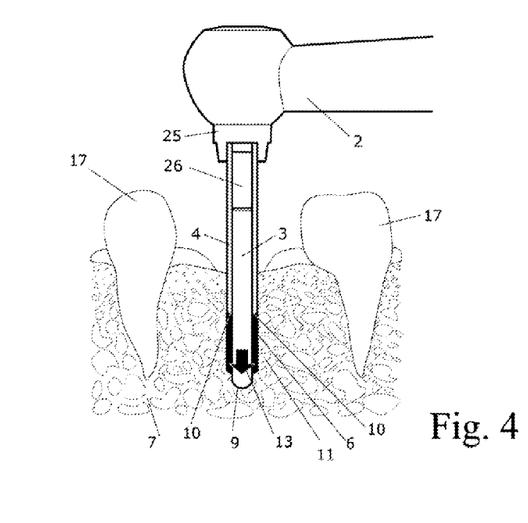
FIG. 4 shows a sectional view according to FIG. 1, phase of inserting the amelioration sleeve into the bore, situation directly before the start of the excitation with the sonotrode.

In the present case where, as has been described above, the drill has generated a tapered bottom area 9 in the recess, the amelioration sleeve 6 is preferably not arranged at the very tip of the guide pin but instead set back slightly from the latter, and the guide pin has an external diameter corresponding substantially to the diameter of the taper 9 in the bottom area. The device 1 that has been made ready in this way is then pushed into the pre-drilled recess 8, as is shown in FIG. 4. The external diameter of the collar 4 is substantially identical to the external diameter D of the amelioration sleeve, and this external diameter is substantially the same as or only very slightly smaller than the internal diameter of the recess generated by the drill. As has been explained above, it is also possible for the external diameter of the collar to be slightly greater than the internal diameter of the recess, such that an additional widening of the recess takes place as the method is carried out.

As can be seen from FIG. 4, the unit comprising guide pin 3, amelioration sleeve 6 and collar 4 can be pushed substantially completely into the recess, and in particular the front tip of the guide pin also penetrates into the tapered bottom area 9, and the front area of the device also completely fills the recesses in the radial direction. This therefore results automatically in an optimal centering or positioning of the device in the recess. The device is thus pushed substantially completely into the recess in the direction of movement 13, without application of ultrasound.

Figure 5:
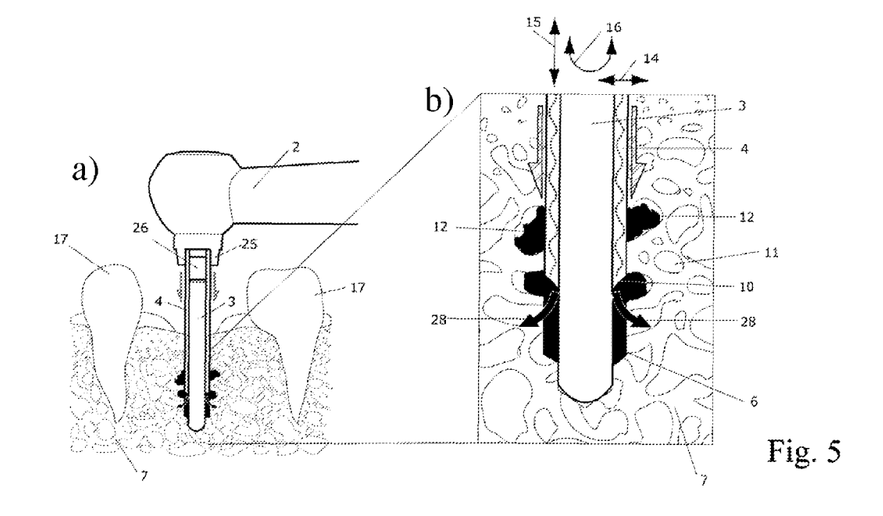
FIG. 5 shows a sectional view according to FIG. 1, phase of the excitation with the sonotrode (intermediate state, with enlarged detail of the tip region), wherein a) shows an overall situation and b) an enlarged detail in the recess region.

It is only now that the ultrasound is switched on, as is shown in FIG. 5. As the device for generating ultrasound, it is possible, for example, to use a device of the E-150 type from Branson Ultrasonics SA (Switzerland) with an operating frequency of 20 kHz and an amplitude of 40 μm at the tip of the sonotrode with an energy of 150 W. The mechanical energy can exert its excitation via the collar, as is preferable, but it is also possible to introduce the energy via the guide pin, or via both the collar and the guide pin. The material of the amelioration sleeve successively liquefies, and at the same time, by pressure on the handle 2, the collar 4 is pushed still further onto the guide pin. As a result of the beveled edge 10 of the collar 4, the liquefied material is now distributed in a very specific manner about the circumference, successively from the top downward, and is introduced into the cavities 11 freed by the recess. The liquefied material is therefore distributed in a very specific manner in the radial direction about the circumference and into these cavities 11, insofar as these have been freed by the drilling, and the mostly disadvantageous movement only toward the bottom of the recess does not take place (which movement is generally problematic in view of the fact that bone material very often becomes more porous with increasing depth). Moreover, the recess is not actually lined by the liquefied material, and instead it is only the undesired cavities adjoining the recess that are as it were filled. Those areas in which the bone already forms a clean border of the recess remain largely uncovered by liquefiable material. By adjusting the angle of the edge 10, it is possible to adjust the radial component, as is shown schematically by the arrows 28.

Figure 6:
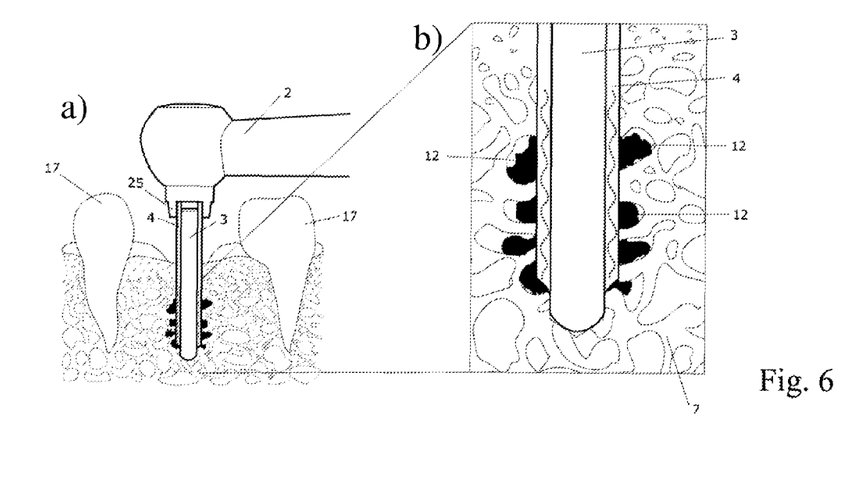
FIG. 6 shows a sectional view according to FIG. 1, phase after the excitation with the sonotrode (final state, with enlarged detail of the tip region), wherein a) shows an overall situation and b) an enlarged detail in the recess region.

In FIG. 6, it is no longer the intermediate state from FIG. 5 that is depicted, but the actual final state in which the collar is pushed onto the guide pin 3 as far as an abutment, and all the material of the amelioration sleeve is distributed into the radially adjoining cavities. It can be seen in particular from the enlarged detail that the material of the amelioration sleeve, in the displaced form 12, is arranged exclusively in the undesired radially adjoining cavities and is not simply transported only toward the bottom. At the exact location where the implant receives its primary stabilization, namely on the circumferential cylinder surface of the recess, a substantially increased contact surface is thereby made available for an anchoring of the implant, and, at the same time, the least possible amount of foreign material is introduced into the bone. The collar does not necessarily have to be pushed on as far as the abutment, and it is also possible to discontinue the process slightly earlier if material of the amelioration sleeve at the bottom is not intended to be displaced in the radial direction.

Figures 7, 8:
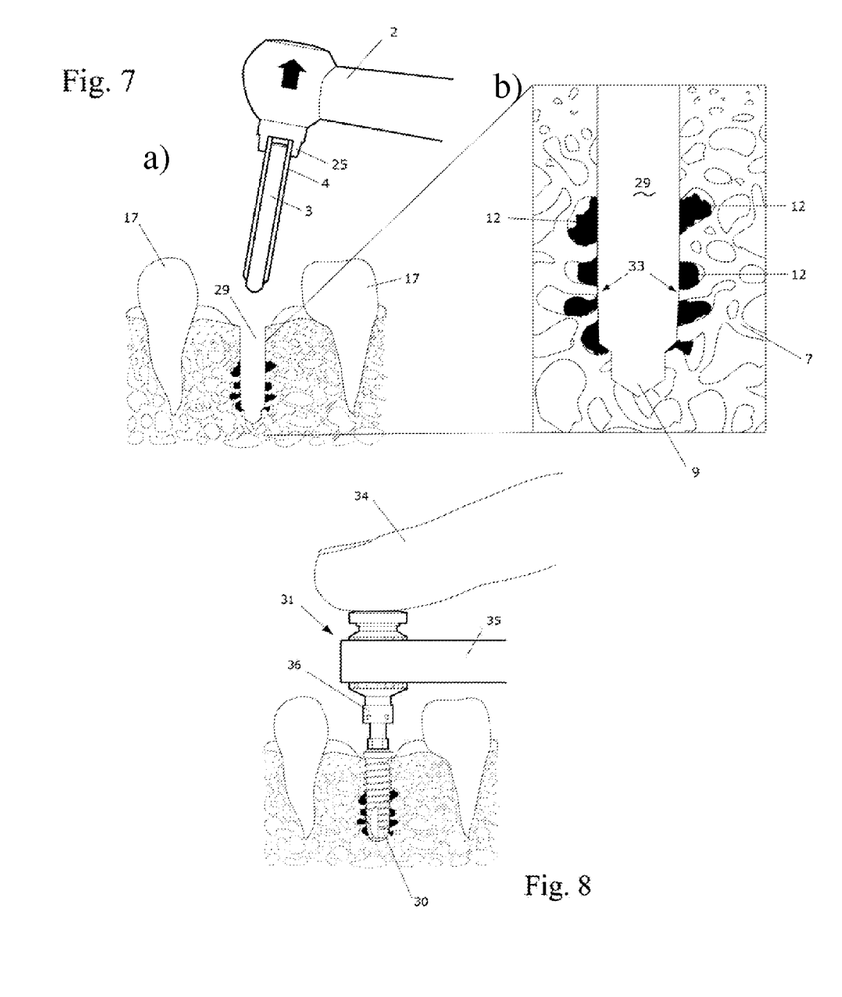
FIG. 7 shows a sectional view according to FIG. 1, state after the excitation with the sonotrode and after removal of the latter from the ameliorated bore (with enlarged detail of the tip region), wherein a) shows an overall situation and b) an enlarged detail in the recess region.
FIG. 8 shows the implant being screwed in manually, supported by a finger.

Thereafter, as is shown in FIG. 7, the tool can be removed from the recess, either with the ultrasound switched on or switched off, and the recess is now ameliorated within the meaning of the invention, as is represented by reference sign 29. This means that the circumferential surface 33 of the ameliorated recess 29 is limited by the liquefiable material, at least in all the places where cavities were adjoining the recess. The liquefiable material does of course solidify again after the ultrasound input has been switched off.

The recess ameliorated in this way can either be left in as it were a sealed state, if such is the aim of the operation, or, as will generally be the case, the actual implant can now be secured in the recess. This step is shown in FIG. 8 for a situation in which a device 31 for screwing in the implant is pressed down by a finger 34 and driven with a torque wrench 35. The actual mounting device 36 is secured on the inner face of the implant 30 and removed again after the mounting procedure. The implant can also be inserted using the handpiece (mechanically). Normally, the sonotrode may not yet be attached.

Figure 9:
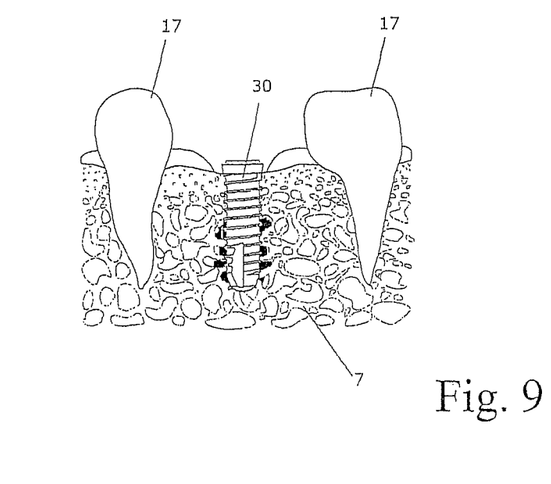
FIG. 9 shows the implant fitted in place.

FIG. 9 shows the implant suitably inserted, and the actual tooth prosthesis, for example, can now be fitted onto such an implant 30.

As was explained at the outset, the proposed method can generally be used in a human tissue area or a human bone, or equally in an animal bone, or generally in a porous material (e.g. wood).

Figure 10:
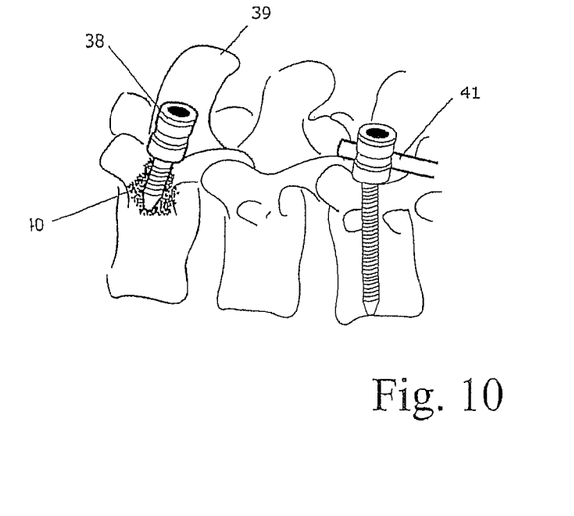
FIG. 10 shows a schematic view of an implant/screw inserted into a similarly ameliorated opening in an area of the spinal column.

FIG. 10 shows an application of the proposed method in connection with spinal column bones 39. Here, a screw 38 instead of a dental implant is inserted into an ameliorated recess 40 (generated by a method analogous to that shown in FIGS. 1 to 7). Such a screw 38 also has a very high primary stability; such a screw can be used, for example, to secure a relative fixing 41.

Figure 11:
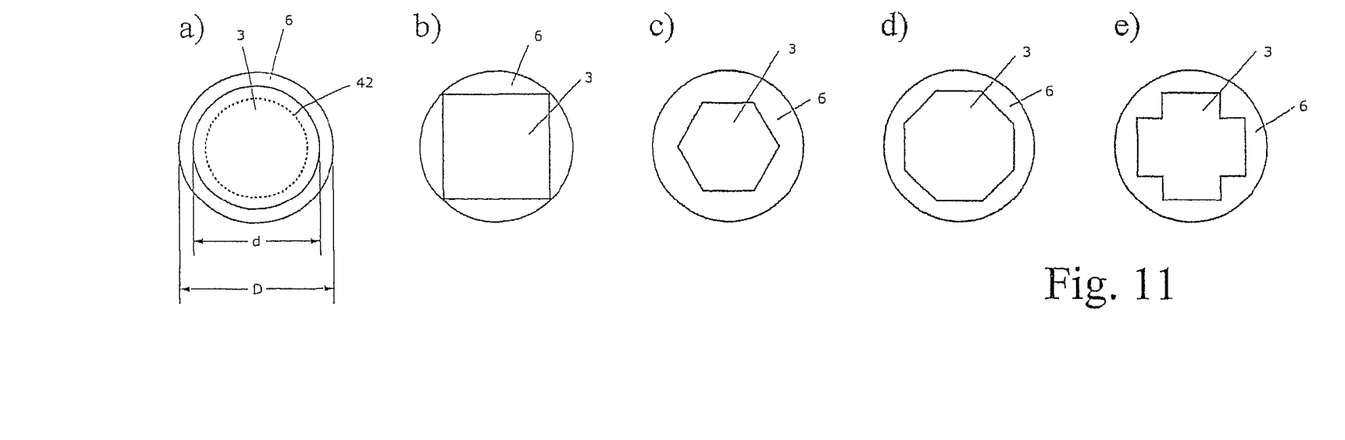

For the sake of completeness, it will also be shown, with reference to FIG. 11, how the amelioration sleeve or guide pin and the collar can be differently configured according to requirements. The normal situation will be the one shown in FIG. 11a). Here, the amelioration sleeve, shown in a section perpendicular to the axis of the guide pin as indicated by A-A in FIG. 3, has an external diameter D and a central recess with an internal diameter d. In this case, it is a relatively thin amelioration sleeve, that is to say a small amount of liquefiable material is made available. The guide pin 3 with an external diameter d is arranged in this amelioration sleeve.

If more liquefiable material is now to be made available, a thinner guide pin 3 and an amelioration sleeve with greater wall thickness can be used, as is indicated by the broken line 42.

Alternative designs of the cross-sectional surface areas of guide pin 3 and amelioration sleeve 6 are shown in FIGS. b)-e). It is in other words possible that the guide pin has, for example, a square cross section, as is shown in FIG. 11b). It can be advantageous in this case if the corners of the square extend almost to the periphery of the amelioration sleeve, although the square can also have a smaller cross-sectional surface area. This is shown for the case of a hexagonal cross-sectional surface area in FIG. 11c), and for a thinner amelioration sleeve and a symmetrical octagonal cross section in FIG. 11d). It is also conceivable to provide other shapes for the cross-sectional surface area of the guide pin 3. For example, FIG. 11e) shows a situation in which the guide pin has a cross-shaped cross-sectional surface area. Such shapes are possible, for example, for the targeted introduction of liquefiable material in directions where there is known to be considerable porosity.

Particularly when the collar 4 is coupled to the sonotrode and transmits the ultrasonic oscillation energy, it can be problematic if the wall thickness of the collar 4 is too small. In these situations, the wall thickness of the collar 4 should lie at least in the range of 0.5-0.8 mm. On the other hand, however, it can happen, for example, that the porosity of the wall of the recess is not particularly pronounced and, accordingly, an amelioration sleeve with such a wall thickness of 0.5-0.8 mm would introduce too much material.

Figure 12:
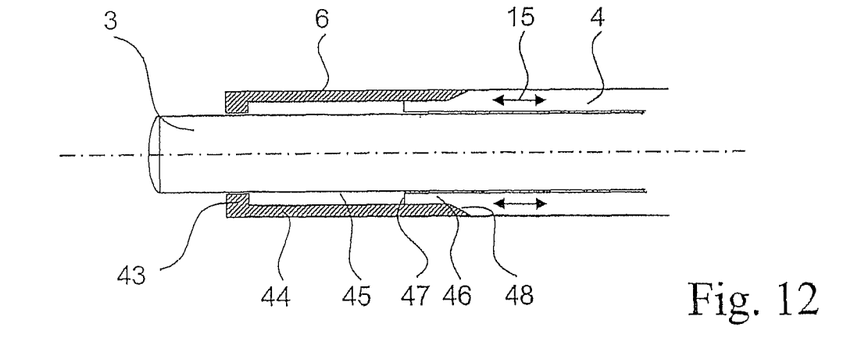
FIG. 12 shows an axial section through a device with an amelioration sleeve having a thin wall thickness.

The illustrative embodiment shown in FIG. 12 is advantageous for such a situation, as is that of FIG. 14 described further below. The amelioration sleeve 6 in this case has, along a wide axial section, a smaller wall thickness than the collar 4. This is achieved by a procedure in which, while leaving an inwardly directed distal flange 43 (the flange can be circumferential, or it can also be formed only in parts in the manner of projections), the inner face of the amelioration sleeve is hollowed out circumferentially (or is not completely hollowed out circumferentially, that is to say, for example, leaving a number of axial webs in contact with the guide pin 3). Thus, a hollow space 45 forms between the guide pin 3 and the now thinner outer wall 44 of the amelioration sleeve. This thin outer wall can have a wall thickness in the range of 0.1-1 mm and can, for example, be easily just 0.1-0.3 mm.

To ensure that the collar 4, in the case of such an amelioration sleeve 6, can still optimally introduce the material of the amelioration sleeve radially into the wall of the recess, the collar 4 is designed, at its distal end, with a tapered cylindrical area 46 having a smaller external diameter. The radial offset of this step at the distal end of the collar 4 corresponds substantially to the wall thickness of the amelioration sleeve in the area 44.

The tapered cylindrical area 46 can be designed narrowing conically at its distal end, although, as is shown in FIG. 12, it can also be designed as a right-angled step.

At the transition from the tapered cylindrical area 46 to the area of the collar 4 arranged behind this with the actual external diameter of the collar, there is a conically tapering area 48.

The tapered cylindrical area 46 accordingly engages with the tip in the hollow space 45 of the amelioration sleeve 6. The proximal end of the amelioration sleeve thus abuts against the inclined flank 48.

If, as is indicated by the arrow 15, ultrasonic oscillation is now introduced in the longitudinal direction via the collar, the amelioration sleeve 6 liquefies basically only in the area of the conical transition 48. By means of the inclined flank in this area 48, the liquefied material is selectively liquefied, exclusively in this area, and distributed radially outward into the peripheral area of the recess and into the porosity present there. On account of the fact that the material of the amelioration sleeve 6 liquefies basically only in the area 48, the small wall thickness of the area 44 is also not generally problematic; despite the small wall thickness there, the amelioration sleeve has virtually no tendency to buckle into the hollow space 45 under the longitudinal pressure, for example.

If the collar is now moved successively leftward in the actual situation in FIG. 12, only the thin wall area 44 liquefies in each case only in the zone 48, and it is only in the zone 48 that the liquefied material is forced radially outward, until the tip 47 abuts against the flange 43. Here, the process can either by discontinued, or further liquefying takes place, now in the bottom area, with slightly more material of the amelioration sleeve. In order to drive the material radially outward in the bottom area too, it is possible, as has already been mentioned, for the area 47 likewise to have a conical shape.

In this construction, the collar 4 is now designed with a small wall thickness only in the very front cylindrical area 46, and this area 46 is also used basically only for guiding, whereas in the area arranged behind this, where the greater forces are present, a greater wall thickness can be used without this also requiring a corresponding wall thickness of the amelioration sleeve 6.

For applications in the dental field, the front cylindrical area 46 typically has a length of circa 0.1-5 mm, preferably 0.1-1 mm or 0.2-0.5 mm in the axial direction, preferably a length of 0.1-0.25 mm.

As has already been explained above, it is also possible that the external diameter of the collar 4 is slightly greater than the original internal diameter of the recess. This is shown by way of example in FIG. 13. Here, the recess in the bottom area 9 is again tapered, and the guide pin 3 protrudes with its distal end into this bottom area. The internal diameter of the recess further to the right in FIG. 13, above this bottom area, corresponds substantially to the external diameter of the amelioration sleeve 6, that is to say the pin 3 and amelioration sleeve 6 can be pushed substantially without resistance into the recess. By contrast, the collar 4 has an external diameter that is slightly greater than the internal diameter of the recess (the diameter is, for example, 0.1-0.2 mm greater than the internal diameter). If the collar 4 is now pressed into the recess, this leads to an enforced widening of the recess, as is indicated schematically by the already widened portion 49.

Figure 13:
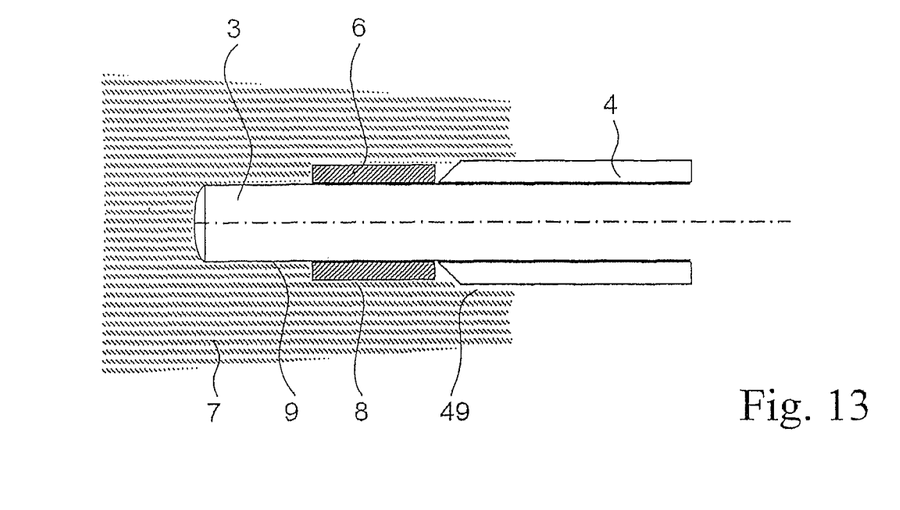
FIG. 13 shows an axial section through a device inserted into a recess which has a smaller internal diameter than the external diameter of the collar.

Such enforced widening by the collar 4 can, for example, be of advantage if, for example, the recess does not have the desired shape and/or the desired diameter and this is to be rectified by the collar 4.

Figure 14A:
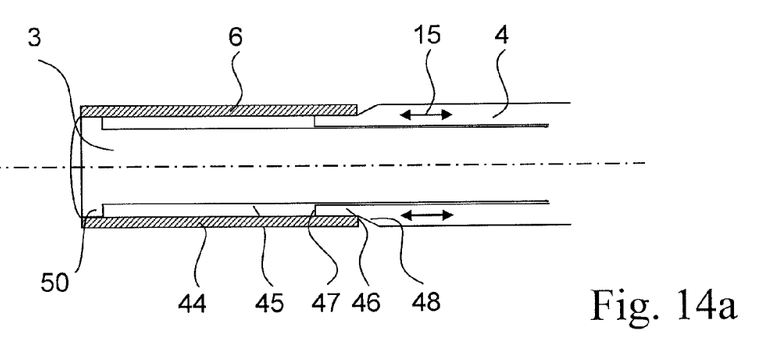
FIG. 14 shows, in each case, an axial section through two further devices with an amelioration sleeve having a thin wall thickness, wherein a) shows a first embodiment and b) a second embodiment.

As a supplement to the illustrative embodiment according to FIG. 12, two further possibilities of the use of a thin amelioration sleeve 6 are shown in FIG. 14. In the illustrative embodiment according to FIG. 14a, the amelioration sleeve 6 is not designed with an inwardly directed distal flange as in FIG. 12, and instead it is designed as a simple hollow cylinder. At its distal end, this hollow cylinder, in the illustrative embodiment according to FIG. 14a, is supported by a flange 50 which is formed integrally on the guide pin or which is secured in the form of a ring thereon. In other words, at the distal end, the amelioration sleeve lies with its inner surface on the outer surface of this flange 50. A similar support to the one in FIG. 12 is thus ensured.

The flange then generally also serves as an abutment for the collar 4.

The flange 50 can be formed all around the circumference, in which case it serves as an abutment for the surface 47 and limits the forward movement of the collar 4. However, the flange 50 can also only form segments. It is then possible to design the tapered area 46 with complementary segments, which then makes it possible, when the collar 4 is advanced fully into the distal area, for these complementary segments of the area 46 to engage through the complementary segments of the flange 50, and as a result the entire material of the amelioration sleeve can be liquefied.

Figure 14B:
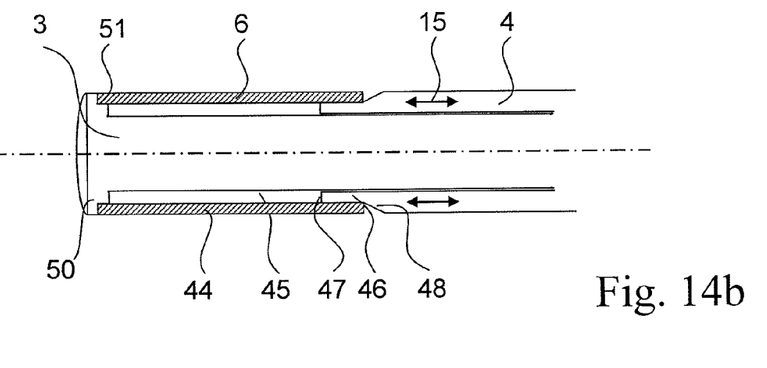

A second illustrative embodiment is shown in FIG. 14b. In this case, the flange 50 has a stepped design on the proximal side. In other words, the flange 50 has an external diameter that corresponds substantially to the external diameter of the collar 4 (it can also be slightly smaller however). On the rear face of the flange 50, the latter is hollowed out circumferentially to form a step 51. The radial depth of this step corresponds substantially to the thickness of the amelioration sleeve 6 (if the external diameter of the flange is slightly less than the external diameter of the collar 4, the depth of the step is also correspondingly smaller). The distal end of the amelioration sleeve 6 thus lies in this step and is supported by this step both in the radially inward direction and also in the forward direction, that is to say toward the distal end. This avoids a situation where, during a forward movement of the collar 4, the amelioration sleeve 6 is pushed over the distal end of the guide pin 3 and is simply pushed into the bottom area of the recess without being liquefied. In the illustrative embodiment according to FIG. 14b also, it is possible for the flange 50 to be designed only in segments and for the area 46 to be configured with complementary segments.

LIST OF REFERENCE SIGNS 1 device
2 handle of 1 with sonotrode
3 guide pin
4 collar
5 edge of 4
6 amelioration sleeve
7 bone
8 bore/recess to be ameliorated in 7
9 tapered bottom area of 8
10 conical tip of 4
11 cavities in 7
12 material of 6 displaced into 11
13 direction of movement of 4 to 3
14 transverse direction of the ultrasonic oscillation
15 longitudinal direction of the ultrasonic oscillation
16 rotational ultrasonic oscillation
17 tooth
18 gum
19 gap
20 drill
21 securing flange for drive of 20
22 drill turns
23 tapering at tip of 20, guide tip
24 drilling direction
25 upper attachment of 4 on 2, rotary attachment, bayonet attachment or snap-fit attachment
26 central recess in 4 for 3
27 upper flank on 6
28 direction of displacement of liquefied material (blue arrows)
29 ameliorated recess in the bone
30 implant
31 device for screwing the implant into ameliorated recess 32 holder
33 circumferential surface of 29
34 finger
35 torque wrench
36 mounting device for implant
37 mounting device for implant with possibility of insertion of sonotrode
38 screw
39 spinal column bone
40 ameliorated recess in 39
41 relative fixing
42 schematic indication (broken line) of a situation for a thicker amelioration sleeve
43 inwardly directed flange of amelioration sleeve
44 thin wall of amelioration sleeve
45 hollow space between guide pin and amelioration sleeve
46 tapered cylindrical area of collar
47 distal end of 46
48 conical transition area to the tapered cylindrical area of the collar
49 already widened portion of the recess
50 support flange on 3
51 proximal step in 50
D external diameter of collar/amelioration sleeve
d external diameter of guide pin or internal diameter of recess in collar and internal diameter of amelioration sleeve

The invention claimed is:

1. A device for the amelioration of a recess, in a porous, perforate material having cavities freed by the recess, said device comprising
an element for generating or coupling in mechanical energy in the form of ultrasonic oscillations in the frequency range of 10 kHz-100 MHz,
a guide pin with a circular cylindrical jacket surface having an external pin diameter and proximal and distal ends,
an amelioration sleeve with a circular cylindrical jacket surface having an external sleeve diameter and proximal and distal ends,
said amelioration sleeve surrounding said guide pin in the area of distal the end thereof directed toward the bottom of said recess and
said amelioration sleeve being made from a material that can be liquefied by mechanical energy in the form of ultrasonic oscillations in the frequency range of 10 kHz-100 MHz,
and a cylindrical collar with a cylindrical jacket surface having an external diameter and having a central recess for receiving said guide pin, wherein said distal end of said guide pin protrudes through, extends past and is uncovered beyond the distal end of the amelioration sleeve,
wherein said guide pin is provided to be inserted as far as the bottom of said recess before mechanical energy is applied, and wherein said uncovered external pin diameter at the distal end of said guide pin and beyond said amelioration sleeve is the same or smaller than in the region where it is surrounded by said amelioration sleeve,
wherein said external sleeve diameter is the same as said external collar diameter, and the same as an internal diameter of the recess to be ameliorated wherein the guide pin is received movably in the central recess such that, when said mechanical energy is applied, the collar can be moved relative to the guide pin in the direction toward the bottom of the recess while liquefying and laterally or longitudinally displacing the material of the amelioration sleeve, and such that the guide pin can be removed with the collar from the recess when the amelioration sleeve has been liquefied and laterally or longitudinally displaced into said cavities freed by the recess, and
wherein said collar, at its distal end, has a circumferential distal edge tapering from said external collar diameter toward said distal end, wherein this distal edge is either straight, and therefore conical, or curved, namely concave or convex, or has a radially stepped design at the distal end, wherein the circumferential distal edge is arranged at the step transition, and wherein said amelioration sleeve is a simple hollow cylinder.

2. The device as claimed in claim 1, wherein the central recess is a circular cylindrical recess which is arranged coaxially with respect to the cylindrical jacket surface, wherein the amelioration sleeve has a circular cylindrical recess for receiving the guide pin, and wherein the guide pin has a circular cylindrical outer surface, wherein the internal diameters of said recesses are the same as the external diameter of the guide pin.

3. The device as claimed in claim 1, wherein the guide pin can be pushed into the collar at most as far as an abutment position, wherein the guide pin, in this abutment position, ends at most flush with the distal end of the collar, or protrudes beyond this end, wherein the protruding length in the abutment position is at least 1-10 mm.

4. The device as claimed in claim 1, wherein the external diameter of the collar is in the range of 1-80 mm, and wherein the external diameter of the guide pin is 0.1-20 mm less, and wherein the amelioration sleeve has a thickness such that the external diameter thereof is the same as the external diameter of the collar.

5. The device as claimed in claim 1, wherein the element generates mechanical energy in the frequency range of 20-150 kHz which are transmitted in the longitudinal, transverse or rotational direction, or in a combination or linear combination of these directions, to the collar or guide pin and thus indirectly to the amelioration sleeve, wherein the collar is optionally secured on a sonotrode, and the guide pin can be moved therein, or the guide pin is secured on the sonotrode, and the collar can be moved, or collar and guide pin are secured on a sonotrode or coupled thereto.

6. The device as claimed in claim 1, wherein the amelioration sleeve is made from a material that can be liquefied by oscillation energy, and that is selected from the following group: thermoplastic biocompatible polymers selected from the group of polyolefins selected from PP, LDPE, HDPE, UHMWPE, polyoxymethylene, polyaryl ether ketones, PAEK, PEEK, PEKK, polycarbonates, polyacrylates, PMMA, polyamides, polyesters, PET, PBT, polysulfones and polyether sulfones, PSU, PES or biodegradable or resorbable polymers, selected from the group of poly(L-lactide) (PLLA), poly(D,L-lactide), or stereocopolymers thereof with a variable ratio of the L and D,L part, polyglycolides (PGA) or copolymers, selected from the group polyglycolide-co-trimethyelene carbonate (PGA-co-TMC), poly(D,L-lactide-co-glycolide), (PDLLA-co-PGA) and poly(L-lactide-co-glycolide) (PLLA-co-PGA), poly(e-caprolactone), polydioxanones, trimethylene carbonates, polyorthoesters (POE) and other polyanhydrides, resorbable polymers which are produced from natural raw materials, namely modified polysaccharides, or a combination or a mixture of these materials, wherein one or more pharmaceutical active substances can optionally also be provided in this material or this material mixture or applied as a layer on this material, wherein these pharmaceutical active substances are released in a controlled manner.

* * * * *